(12) United States Patent
Sinn et al.

(10) Patent No.: US 7,803,791 B2
(45) Date of Patent: Sep. 28, 2010

(54) METHOD FOR PRODUCING ALBUMIN CONJUGATES CONTAINING GYRASE INHIBITORS

(75) Inventors: Hannsjörg Sinn, Wiesloch (DE); Marcel Mülbaier, Heidelberg (DE)

(73) Assignee: Albupharm Heidelberg GmbH & Co. KG, Heidelberg (DE)

( * ) Notice: Subject to any disclaimer, the term of this patent is extended or adjusted under 35 U.S.C. 154(b) by 141 days.

(21) Appl. No.: 11/795,721

(22) PCT Filed: Jan. 20, 2006

(86) PCT No.: PCT/EP2006/000519

§ 371 (c)(1),
(2), (4) Date: Jul. 20, 2007

(87) PCT Pub. No.: WO2006/077146

PCT Pub. Date: Jul. 27, 2006

(65) Prior Publication Data

US 2008/0108708 A1    May 8, 2008

(30) Foreign Application Priority Data

Jan. 21, 2005  (DE) ...................... 10 2005 002 991

(51) Int. Cl.
*A61K 31/47* (2006.01)
*A61K 38/38* (2006.01)
*A61K 47/48* (2006.01)
*C07K 14/76* (2006.01)
*C07K 14/765* (2006.01)
*C07D 215/00* (2006.01)
*A61P 29/00* (2006.01)
*A61P 35/00* (2006.01)

(52) U.S. Cl. ...................... 514/187; 514/303; 514/311; 544/128; 544/363; 546/1; 546/7; 546/134; 546/152; 530/362; 530/363

(58) Field of Classification Search ........................ None
See application file for complete search history.

(56) References Cited

U.S. PATENT DOCUMENTS 6,984,652 B2 *  1/2006  Yager et al. ................. 514/365
2003/0203917 A1  10/2003  Erskine et al.

FOREIGN PATENT DOCUMENTS

WO    00/76511 A    12/2000

OTHER PUBLICATIONS

Duan J and Yuan Z, "Development of Indirect Competetive ELISA for Ciprofloxacin Residues in Food Animal Edible Tissues," J. Agric. Food Chem., 2001, 49: 1087-1089.*
Zhou D-Y, Qi X-Y, Chen S-S, Zhou P-G, "The Synthesis of norfloxacin-bovine serum albumin and norfloxacin-ovalbumin conjugates," Journal of Shanghai Fisheries University, Dec. 2002, 11(4): 362-366, Chinese with English abstract.*
Partial translation of "U" above from STIC. Jun. 18, 2009.*
Tanitame A, Oyamada Y, Ofugi K, Suzuki K, Ito H, Kawasaki M, Wachi M, Yamagishi J-I, "Potent DNA gyrase inhibitors: novel 5-vinylpyrazole analogues with Gram-positive antibacterial activity," Bioorganic & Medicinal Chemistry Letters, 2004, 14: 2863-2866.*
Derivative and analog definition from http://cancerweb.ncl.ac.uk/cgi-bin/omd?query=derivative, pp. 1-5. Accessed Jul. 7, 2005.*
International Search Report and International Preliminary Report on Patentability (Chapter II of the Patent Cooperation Treaty) for PCT/EP2006/000519, Dec. 10, 2007.
Fish, et al., "The Clinical Pharmacokinetics of Levofloxacin", U.S. National Library of Medicine in Bethesda, MD, USA, Feb. 1997 and Clinical Pharmacokinetics, vol. 32, No. 2, pp. 101-119, 1997.
Aboul-Fadl, et al., "Synthesis and In Vitro Investigations of Nalidixic Acid Amides of Amino Acid Esters as Prodrugs", Pharmazie, Die, Govi Verlag, vol. 51, No. 1, pp. 30-33, 1996.
Holtzapple, et al., "Production and Characterization of Monoclonal Antibodies Against Sarafloxacin and Cross-Reactivity Studies of Related Fluoroqionolones", Journal of Agricultural and Food Chemistry, vol. 45, No. 5, pp. 1984-1990, 1997.
Hammer, et al., "Antibody-Capture Immunoassay for the Detection of Enforloxacin in Raw Milk", Milchwissenschaft, vol. 50, No. 9, pp. 513-514, 1995.
Kidwai, et al., "The Fluorinated Quinolones", Current Pharmaceutical Design, vol. 4, No. 2, pp. 101-118, 1998.
Kratz, "Drug Conjugates with Albumin and Transferrin", Expert Opinion on Therapeutic Patients, vol. 12, No. 3, pp. 433-439, 2002.
Stehle, et al., "The Loading Rate Determines Tumor Targeting Properties of Methotrexate-Albumin Conjugates in Rats", Anti-Cancer Drugs, vol. 8, No. 7, pp. 677-685, 1997.
Davis, et al., "A Simple Modified Carbodimide Method for Conjugation of Small-Molecular-Weight Compounds to Immunoglobulin G with Minimal Protein Crosslinking", Analytical Biochemistry, vol. 116, No. 2, pp. 402-407, 1981.

* cited by examiner

*Primary Examiner*—Julie Ha
(74) *Attorney, Agent, or Firm*—Ping Wang; Morris, Manning & Martin LLP

(57) ABSTRACT

The present invention is directed to a Gyrase inhibitor-protein conjugate; in particular a Gyrase inhibitor-albumin conjugate. The present invention further provides methods of the treatment of inflammatory conditions and tumors. Methods of making and producing a Gyrase inhibitor-protein conjugate are also disclosed.

13 Claims, 2 Drawing Sheets

METHOD FOR PRODUCING ALBUMIN CONJUGATES CONTAINING GYRASE INHIBITORS

FIELD OF THE INVENTION

The present invention concerns gyrase inhibitor-protein conjugates and in particular gyrase inhibitor-albumin conjugates, pharmaceutical preparations comprising gyrase inhibitor-protein conjugates in particular for the treatment and/or prophylaxis of inflammatory processes and/or tumours as well as methods for their production.

BACKGROUND OF THE INVENTION

Gyrase inhibitors are antibiotics which block the enzyme DNA gyrase which is a member of the topoisomerase 2 family. These enzymes fold the DNA helix on the surface of RNA cores to form loops and the loops are at the same time additionally twisted into a spiral. This results in an arrangement which requires a minimum amount of space. At the same time rapid replication, transcription and recombination of the DNA is promoted by this arrangement. If the function of this enzyme is inhibited or completely blocked by an active substance, a central, vitally important site of the dividing cell is affected and it is no longer viable.

Previously various fluorine-containing gyrase inhibitors have been used in their low-molecular form such as e.g. norfloxacin, enoxacin or ciprofloxacin to treat bacterial inflammations. A disadvantage of previous treatments using gyrase inhibitors is in particular the short retention time of the substances in the circulation so that they only have a very narrow time window to develop their activity. This is a fundamental problem of drug treating a disease with gyrase inhibitors which is based on a rapid renal and hepatobiliary elimination. Thus, for example after an oral dose of 400 mg norfloxacin a maximum of 1 µg/ml blood would be expected within a period of one hour which corresponds to an available amount of 1 to 2% of the administered total dose. Another disadvantage of the previously used gyrase inhibitors is that only a small proportion of the administered drug reaches the target site. This results in undesired side-effects which are mainly due to the fact that by far the largest proportion of the active substances is taken up by healthy organs where they cause side-effects. Observed side-effects are for example complaints in the area of the gastrointestinal tract, of the circulation and of the peripheral and central nervous system such as heightened excitability, restlessness, sleep disorders, disorientation and even to the extent of hallucinations and cramps as well as drowsiness extending to psychotic conditions. In addition skin disorders especially due to photosensitization as well as disorders of blood cell formation such as for example thrombocytopenia, leucopenia etc. have been observed.

P. Hammer and W. Heeschen ("Milchwissenschaft" 1995, 50(9), p. 513-514) disclose a method for producing an enrofloxacin-bovine serum albumin conjugate using N-hydroxysuccinimide, anhydrous dimethylformamide and dicyclohexyl-carbodiimide (DCC). The conjugate is used as an immunogen to produce antibodies and the antibody which is specific for enrofloxacin and ciprofloxacin is used in an indirect competitive immunoassay (ELISA). A major disadvantage of the conjugate disclosed by Hammer and Heeschen et al. is, however, the stated high molar ratio of enrofloxacin to bovine serum albumin which is about 25:1 because with such a high loading one can on no account assume that the protein is in its natural form but rather that the protein is massively denatured. However, this denaturation was the aim of Hammer and Heeschen because the immunization to obtain antibodies can only be successfully carried out with such a denatured protein. Thus, a denatured product that can no longer be administered is present which does not come into consideration for clinical use. It can no longer be ensured that the active substance is released directly at the site of action and is thus free of side-effects. Hence, the conjugate disclosed by Hammer and Heeschen is used exclusively in vitro to detect the gyrase inhibitors enrofloxacin and ciprofloxacin in the raw milk of cows.

SUMMARY OF THE INVENTION

Hence, one object of the present invention was to provide gyrase inhibitors in a form in which the difficulties occurring in the prior art can be overcome and which in particular allows a specific uptake into bacterially inflamed tissue and/or tumour tissue with at the same time a long half-life, low dosage and the associated low side-effects in the organism.

EXEMPLARY EMBODIMENTS OF THE INVENTION

Figure 1:
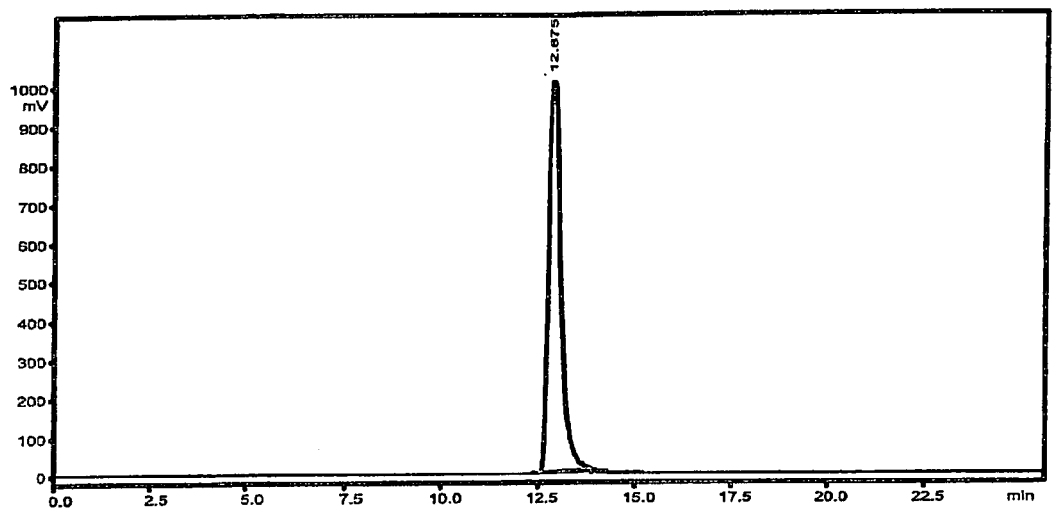
FIG. 1 shows a HPLC chromatogram of norfloxacin alone.

This object is achieved according to the invention by providing a gyrase inhibitor-protein conjugate which comprises a gyrase inhibitor and a protein. The gyrase inhibitor-protein conjugate is particularly preferably a gyrase inhibitor-protein conjugate comprising a gyrase inhibitor and a protein which is characterized in that the molar ratio of gyrase inhibitor: protein is 2:1 to 0.1:1.

By coupling gyrase inhibitors to proteins in particular to carrier proteins, the low-molecular active substances which as such are eliminated rapidly from the body are hidden from the excretion and capture mechanisms of the body and a long half-life and thus a high bioavailability in the body is achieved. This allows small amounts of active substance to be administered and thus substantially reduces side-effects that may occur.

Toxic effects on healthy tissue or organs is virtually not observed because normal healthy cells have no need to take up protein. In contrast proteins and in particular carrier proteins are taken up by cells associated with inflammatory processes or by proliferating tumour cells and thus lead to a targeted accumulation of active substance in these cells.

Albumin and in particular serum albumin and most preferably human albumin or human serum albumin (HSA) is preferably used as a protein in the conjugates according to the invention.

Basically a protein is preferably used which is native to the patient for whom the conjugate is provided. A native protein is understood as a protein which is derived from the same species as the species to which the protein is administered. This for example means that in the case of administration to humans, human proteins are used and in the case of administration to mice corresponding mouse proteins are used etc.

Human albumin is an endogenous, ubiquitously distributed and non-immunogenic protein. It has a molecular weight of about 68 kDa and is thus not eliminated by the kidney. Albumin constitutes approximately 60% of the total amount of plasma protein. In the healthy organism it fulfils among others transport functions for many substances and in an acute emergency serves as a reserve energy carrier which is available overall and at any time in the organism.

It is not taken up by healthy body tissue under physiological conditions. In contrast cells associated with inflammatory and in particular with bacterial processes and cells associated with tumours and in particular solid tumours have a high turnover of proteins and in particular of plasma proteins, mainly of albumin. Albumin is degraded by this mechanism in the target cells where the protein serves as an energy supply and the active substance is released. This means that a specific uptake and thus an accumulation of the active substance at the target site can be achieved by coupling gyrase inhibitors to proteins, in particular albumin according to the invention. As a result of this targeted accumulation, it is possible to substantially reduce the dose of active substance which facilitates a treatment that is low in side-effects because the active substances are now only released in the area of the inflammatory process or in proliferating tumour cells due to enzymatic cleavage of the protein whereas the conjugate in not taken up by other healthy body tissue. Another advantage of albumin is that it is available at any time also in large amounts in a clinically usable form.

The biokinetic properties and thus also the biological half-life of the conjugate according to the invention is solely determined by the macromolecule albumin but not by the low-molecular gyrase inhibitor. As a result the initially available concentration of active substance does not fall to about 50% of the initial value until after approximately twenty days. The long biological half-life of the albumin conjugates substantially widens the previously very narrow time window of active substance availability without further side-effects occurring. Subsequent medications are only required at an interval of two to three weeks. The protein used to form the conjugates according to the invention preferably has a molecular weight of $\geq 18000$ Da, particularly preferably of $\geq 30000$ Da and most preferably of $\geq 50000$ Da.

The gyrase inhibitor is coupled to the carrier protein which is preferably albumin without limiting the biological activity of the active substance and without loss of the natural character of the protein used as a carrier and in particular of the albumin. A protein which is present in its natural form is understood in particular as a non-denatured, non-altered protein and in particular a protein whose properties such as for example its structure, its physicochemical properties etc. are unchanged. In the conjugates the molar ratio of active substance to carrier protein is 2:1 to 0.1:1, preferably 1.5:1 to 0.2:1 and particularly preferably 1.1:1 to 0.5:1. Thus, for example albumin when loaded 1:1 with a gyrase inhibitor still exhibits biologically active behaviour.

The active substance is particularly preferably covalently coupled to the carrier protein. Furthermore, the covalent coupling is preferably selected such that it can be cleaved again in pathologically altered tissues so that the biological activity of the original active substance is preserved and can be utilized. It is preferably enzymatically cleaved. In this connection the protein can either be bound directly or via a linker.

A direct covalent coupling of the active substance to the carrier protein is especially preferred. A direct covalent coupling of the active substance to the carrier means that the active substance is bound to the transport protein by a linker-free or spacer-free bond. The gyrase inhibitor is preferably covalently bound to the protein by means of an acid amide bond that is formed from a carboxyl group of the gyrase inhibitor and an amino group, preferably a lysine group of the protein.

Use of gyrase inhibitors which are selected from the group consisting of quinolone carboxylic acid derivatives, 1,8-naphtyridine derivatives, pyridopyrimidine carboxylic acid derivatives and/or cinnolone carboxylic acid derivatives has proven to be particularly suitable.

In a preferred embodiment of the present invention suitable quinolone carboxylic acid derivatives are selected from the group consisting of ciprofloxacin, enoxacin, norfloxacin, ofloxacin, oxolinic acid, sparfloxacin, pefloxacin, fleroxacin, temafloxacin, lomifloxacin, ibafloxacin, marbofloxacin, danofloxacin, moxifloxacin, nadifloxacin, enrofloxacin, sarafloxacin and/or gatifloxacin; nalidixic acid is a suitable 1,8-naphtyridine derivative; suitable pyridopyrimidine carboxylic acid derivatives are selected from the group consisting of pipemidic acid and/or piromidic acid, and suitable cinnolone carboxylic acid derivatives are selected from the group consisting of rosoxacin and/or cinoxacin.

The gyrase inhibitors norfloxacin, enoxacin and/or ciprofloxacin and especially preferably norfloxacin are particularly preferably bound to a carrier protein according to the invention.

Low-molecular gyrase inhibitors are particularly preferably bound to the transport protein within the scope of the present invention because in this manner the macromolecule albumin alone determines the biokinetic properties but not the low-molecular gyrase inhibitor. The gyrase inhibitor used according to the invention to form the conjugates preferably has a molecular weight of <2000 Da, particularly preferably of <1000 Da and most preferably of <500 Da.

In a preferred embodiment the active substance conjugate according to the invention is preferably in a pharmaceutical preparation. Such a pharmaceutical preparation in particular has low side-effects and can for example also be administered to out-patients. It is preferably administered intravenously.

A dosage unit preferably contains 1 to 5 mg gyrase inhibitor active substance per kilogram body weight per 2 to 3 weeks and in particular 1 to 2 mg active substance per kilogram body weight per 2 to 3 weeks. The dose can in particular be selected to be less than that used for conventional treatment with gyrase inhibitors and is preferably $\leq 2$ mg and particularly preferably $\leq 1$ mg active substance gyrase inhibitor per kilogram body weight per 2 to 3 weeks.

While it is possible to administer one dosage unit per day, it is also possible due to the long biological half-life of the conjugates in the body to stipulate longer time intervals between administrations so that a dosage unit is administered at most every two days, particularly preferably at most every five days, especially preferably at most every seven days and most preferably every 14 to 21 days.

In a preferred embodiment of the present invention the gyrase inhibitor-protein conjugate is used to produce a pharmaceutical preparation for the treatment and/or prophylaxis of inflammatory processes, in particular of bacterial inflammations and/or tumours, in particular solid tumours. In this case the pharmaceutical preparation is preferably administered to mammals, humans and/or animals and in particular to humans.

The conjugates according to the invention can be used to treat inflammatory processes and tumours. Bacterial inflammations which can be treated according to the invention are for example infections of the kidney, urinary tract, genital organs, respiratory tract, abdominal space and skin. In this process pathogens such as for example *Haemophilus influencae, Haemophilus ducreyi, Ulcus molle*, legionellae, brucellae, *chlamydia*, mycoplasmas/ureaplasmas, mycobacteria such as for example *Mycobacterium tuberculosis* and/or gram-negative rod-shaped bacteria including many

*Pseudomonas aeruginosa* strains, gram-negative cocci, enteritis pathogens such as for example salmonellae, shigellae, yersiniae and/or camphylobactor are treated in this connection according to the invention.

Furthermore, it is possible to use the conjugates according to the invention in a combination therapy for example together with other antibacterial and/or anti-tumoral agents. The doses of the respective components are further reduced in such a combination therapy.

Another subject matter of the present invention is a method for producing a gyrase inhibitor-protein conjugate comprising reacting a gyrase inhibitor, preferably a low-molecular gyrase inhibitor with a protein, preferably with a high-molecular carrier protein. A method for producing a gyrase inhibitor-protein conjugate comprising reacting a gyrase inhibitor with a protein in which the molar ratio of gyrase inhibitor:protein is 2:1 to 0.1:1 is particularly preferred within the scope of the present invention.

The gyrase inhibitor is preferably covalently coupled to the protein for example albumin without limiting its natural character. A coupling has proven to be particularly advantageous in which firstly a succinimidyl ester is formed from the low-molecular gyrase inhibitor by means of a carbodiimide and subsequently the succinimidyl ester of the gyrase inhibitor is reacted with a protein.

An efficient covalent coupling of the active substance to the carrier molecule (i.e. to the protein) is important for the production of the conjugates that are used according to the invention. In particular undesired changes of the carrier protein or/and of the active substance should not occur during the coupling. Conventional activation of organic compounds containing carboxyl groups with dicyclohexyl carbodiimide (DCC) requires more than 12 hours at room temperature or at +4° C. (P. Hammer and W. Heeschen ("Milchwissenschaft" 1995, 50(9), p. 513-514), DP 41 22 210 A1; EP 0 879 604 A1; EP 0 820 308). Furthermore, insoluble substances are formed during the activation in this method some of which already precipitate during the activation and some of which precipitate when the activated active substance is introduced into an aqueous protein solution and have to be separated by time-consuming and expensive filtration steps that are never 100% (due to the lipophilic domains in albumin) in addition to the actual product purification in order that the conjugate can be administered for medical purposes.

There was therefore a need to provide a method for producing active substance-protein conjugates in which these problems do not occur and in which in particular no water-insoluble byproducts are formed.

This object was achieved according to the invention by a method for producing a conjugate in which a gyrase inhibitor and a protein are reacted in the presence of N-(3-dimethylaminopropyl)-N'-ethylcarbodiimide (EDC) as the carbodiimide and N-hydroxysuccinimide.

Surprisingly it was found that EDC especially in the form of a hydrochloride can be used to activate the organic compound containing carboxyl groups and to react it with a carrier protein without formation of water-insoluble byproducts which would have had to be separated in a time-consuming and costly manner. Intermediate purification steps become redundant in this method and the preparation time and thus also the production costs are substantially reduced. Furthermore, problems which are caused by insoluble substances or byproducts are avoided when the conjugate is injected into a human or animal body.

The activation preferably takes place at a temperature of 10 to 100° C., more preferably of 20 to 90° C. and even more preferably of 50 to 75° C. for a reaction time of 1 minute to 10 hours, more preferably of 20 to 50 minutes. The activated active substance is reacted with the carrier protein preferably at a temperature between 10 and 50° C. in particular between 20 and 40° C.

The carboxyl-containing compound in particular norfloxacin is preferably activated with EDC and N-hydroxysuccinimide in an organic solvent, preferably in dimethyl sulfoxide (DMSO). Further suitable organic solvents are for example dimethyl acetamide or dioxane. The activation is preferably carried out while excluding water in particular in the presence of ≦5% by weight water, more preferably of ≦1% by weight water and most preferably completely anhydrously.

A major advantage of the production method according to the invention is that the activation reagents that are used i.e. EDC and N-hydroxysuccinimide are highly water-soluble. Consequently coupling reagents that are not used in the reaction can be removed from the product obtained in a simple manner for example by washing with water. In contrast an inseparable residue of coupling reagent remains in the conjugate in the case of the coupling reagents used in the prior art for example when using dicyclohexyl carbodiimide (DCC). Thus, when using DCC for a gyrase inhibitor-albumin conjugate, an inseparable residue of about 13 to 15% by weight DCC is observed in the conjugate which is probably bound to a lipophilic domain in the albumin. This residue can only be detected with the aid of HPLC and can only be preparatively separated by a considerable amount of effort.

If a high excess of DCC in relation to the active substance to be coupled is additionally used as described in the publication by P. Hammer and W. Heeschen (see above), i.e. a molar ratio of DCC:active substance of about 10:1, it is no longer possible to completely separate the protein by means of dialysis or ultrafiltration. However, this DCC which adheres to the protein and is still reactive leads in the course of time to a progressive alteration of the protein due to intramolecular and intermolecular cross-linking resulting in a time-dependent change in the properties of the carrier protein. Hence, a conjugate produced in this manner does not come into consideration for a clinical application.

Another preferred aspect of the invention concerns an optimized production method for a conjugate according to the invention comprising the reaction of a gyrase inhibitor with albumin by a direct covalent coupling characterized in that a gyrase inhibitor and albumin are reacted in the presence of a carbodiimide, preferably in the presence of N-(3-dimethylaminopropyl)-N'-ethylcarbodiimide without N-hydroxysuccinimide or N-hydroxysuccinamide or any other activation reagent.

In a preferred embodiment the gyrase inhibitor is preferably a gyrase inhibitor selected from the group consisting of quinolone carboxylic acid derivatives, 1,8-naphtyridine derivatives, pyridopyrimidine carboxylic acid derivatives and/or cinnolone carboxylic acid derivatives. The quinolone carboxylic acid derivatives are particularly preferably selected from the group consisting of ciprofloxacin, enoxacin, norfloxacin, ofloxacin, oxolinic acid, sparfloxacin, pefloxacin, fleroxacin, temafloxacin, lomifloxacin, ibafloxacin, marbofloxacin, danofloxacin, moxifloxacin, nadifloxacin, enrofloxacin, sarafloxacin and/or gatifloxacin. The 1,8-naphtyridine derivative is preferably nalidixic acid and the pyridopyrimidine carboxylic acid derivatives are preferably selected from the group consisting of pipemidic acid and/or piromidic acid and the cinnolone carboxylic acid derivatives are particularly preferably selected from the group consisting of rosoxacin and/or cinoxacin. The gyrase inhibitors are particularly preferably norfloxacin, enoxacin and/or ciprofloxacin and especially preferably norfloxacin. The protein is preferably albumin.

Surprisingly it was found that the optimized method which does not use N-hydroxysuccinimide or N-hydroxysuccinamide or other additional activation reagents has a positive effect on the purification procedure and thus facilitates the production. Using EDC for activation without adding N-hydroxysuccinimide (HSI), the time to activate norfloxacin is much less than the required 30 minutes when using HSI. A further advantage of the optimized method is that after adding the activated active substance to the protein added first, in particular albumin, without H-hydroxysuccinimide it is possible to directly monitor the coupling efficiency. When using N-hydroxysuccinimide it also has a high UV absorption in the HPLC when the UV measuring cell is adjusted to 280 nm and interferes or makes it more difficult to directly determine the coupling yield due to its retention time of about 11.5 minutes at which other low-molecular compounds also appear. This means that in many cases it is not possible to determine the yield until the purification of the conjugate is completed. This factor can now be excluded by the optimized method which does not use N-hydroxysuccinimide. This is also a major advantage for the product safety. Another advantage of the optimized method is that the coupling yield is surprisingly 98 to 99% on average.

Consequently the total costs of the respective conjugate are considerably reduced by this simplification of the production.

The conjugates produced by the method according to the invention can, due to their high purity, be provided for numerous uses and in particular for an intravenous administration. Thus, for example when using a gyrase inhibitor having an anti-inflammatory effect or anti-tumoral action, such conjugates can be used advantageously to produce pharmaceutical preparations for the prophylaxis and/or for the treatment of inflammatory processes and in particular to produce a pharmaceutical preparation for treating bacterial inflammations or for treating solid tumours.

Figure 2:
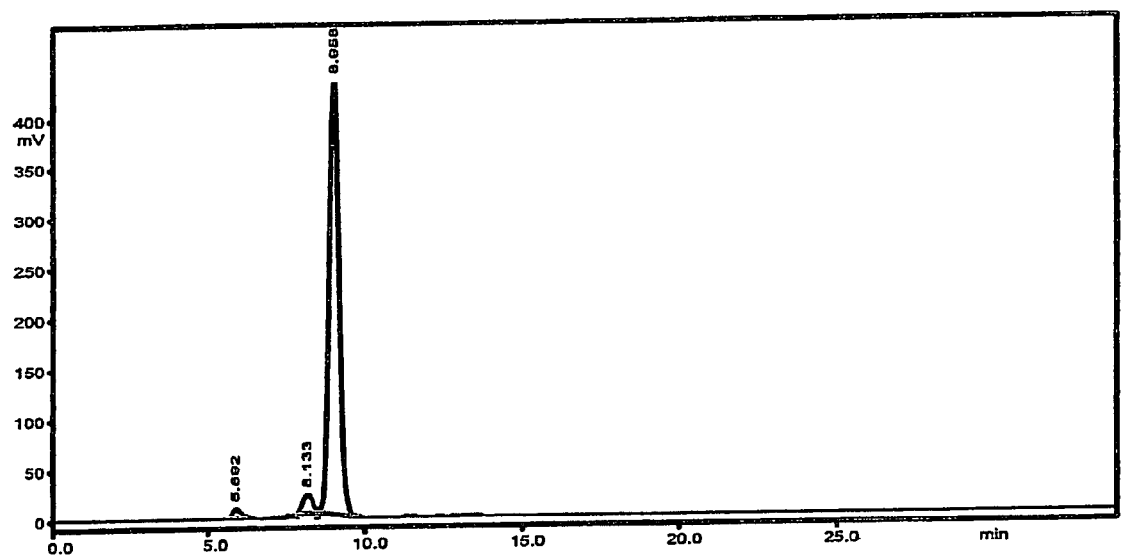
FIG. 2 shows the chromatogram of the norfloxacin-HSA conjugate produced according to example 1.

The invention is further elucidated by the following example and the attached figures. FIG. 1 shows a HPLC chromatogram of norfloxacin alone and FIG. 2 shows the chromatogram of the norfloxacin-HSA conjugate produced according to example 1.

Example 1

Norfloxacin-HSA Conjugate

Starting Materials:

Norfloxacin (SIGMA-ALDRICH, Taufkirchen), N-(3-dimethylaminopropyl)-N'-ethylcarbodiimide hydrochloride (SIGMA-ALDRICH, Taufkirchen), N-hydroxysuccinimide (SIGMA-ALDRICH, Taufkirchen) and albumin (Göricke, Dessau).

Instead of norfloxacin it is also possible to use other gyrase inhibitors containing carboxyl groups for the conjugation with albumin or with another protein of choice.

Standard Preparation on a Laboratory Scale:

About 12.2 mg norfloxacin (MW 319.3) is placed first together with about 14.6 mg N-(3-dimethylaminopropyl)-N'-ethylcarbodiimide hydrochloride (MW 191.71, molar ratio 1:2) and about 44 mg N-hydroxysuccinimide (MW 115.9, molar ratio 1:10) in a test tube with an NS 14.5 ground joint and stopper. After adding 1 ml dimethylsulfoxide (DMSO) or similar polar solvents, the reaction mixture is placed in a water bath preheated to 65° C. After a reaction time of about 30 minutes, a clear colourless solution of norfloxacin succinimidyl ester is present which, after cooling to room temperature, is added very slowly to a 5% albumin solution. A turbidity is briefly formed at the point of entry which, however, rapidly redissolves.

The control chromatogram can be prepared directly after the coupling.

The undesired accompanying substances DMSO, NHS, N-(3-dimethylamino-propyl)-N'-ethyl urea and non-covalently bound norfloxacin in the final product are separated by ultrafiltration (YM 30, Millipore).

Quality Control (HPLC/SEC):

Precolumn: Reprosil 200 SEC 5×4 mm, 5 μm (Dr. Maisch GmbH)

Column: Reprosil 200 SEC 300×4.6 mm, 5 μm (Dr. Maisch GmbH)

Solvent: 0.18 M $Na_2HPO_4$; pH 7.4; 5% methanol

Flow rate: 0.3 ml/min

Pressure: about 50 bar

UV-vis: 280 nm

Retention Times:

oligomeric albumin fraction 5.90 min dimeric albumin fraction 8.14 min monomeric albumin fraction 8.96 min free norfloxacin 12.88 min Chromatograms: see FIGS. 1 and 2

The invention claimed is:

1. A Gyrase inhibitor-albumin conjugate comprising a gyrase inhibitor and an albumin, wherein the molar ratio of the gyrase inhibitor to the albumin is 2:1 to 0.1:1 wherein the conjugate is obtained by reacting the gyrase inhibitor and the albumin in the presence of N-(3-dimethylaminopropyl)-N'-ethyl-carbonyldiimide in an organic solvent, and wherein the gyrase inhibitor compound comprises a carboxylic acid group which links the gyrase inhibitor via an amide bond to the albumin, wherein the gyrase inhibitor is selected from the group consisting of quinolone carboxylic acid derivatives, 1,8-naphtyridine derivatives, pyridopyrimidine carboxylic acid derivatives and cinnolone carboxylic acid derivatives, wherein said quinolone carboxylic acid derivative selected from the group consisting of ciprofloxacin, enoxacin, norfloxacin, ofloxacin, oxolinic acid, sparfloxacin, pefloxacin, fleroxacin, temafloxacin, lomifloxacin, ibafloxacin, marbofloxacin, danofloxacin, moxifloxacin, nadifloxacin, enrofloxacin, sarafloxacin and gatifloxacin;

wherein said 1,8-naphtyridine derivative is a nalidixic acid;

wherein said pyridopyrimidine carboxylic acid derivative selected from the group consisting of pipemidic acid and piromidic acid; and wherein said cinnolone carboxylic acid derivative selected from the group consisting of rosoxacin and cinoxacin.

2. The Gyrase inhibitor-albumin conjugate according to claim 1, wherein the albumin is a human serum albumin.

3. The Gyrase inhibitor-albumin conjugate according to claim 1, wherein the albumin is present in a native form.

4. The Gyrase inhibitor-albumin conjugate according to claim 1 wherein the gyrase inhibitor is covalently coupled to the albumin.

5. The Gyrase inhibitor-albumin conjugate according to claim 4, wherein the covalent coupling is cleavable under pathological conditions.

6. The Gyrase inhibitor-albumin conjugate according to claim 5, wherein the cleavage takes place enzymatically.

7. The Gyrase inhibitor-albumin conjugate according to claim 1, wherein the albumin is present in its natural form.

8. The Gyrase inhibitor-albumin conjugate according to claim 1, wherein the gyrase inhibitor is selected from the group consisting of norfloxacin, enoxacin and ciprofloxacin.

9. The Gyrase inhibitor-albumin conjugate according to claim 8, wherein the gyrase inhibitor is norfloxacin.

10. The Gyrase inhibitor-albumin conjugate according to claim 1, wherein the gyrase inhibitor has a molecular weight of <2000 Da.

11. The Gyrase inhibitor-albumin conjugate according to claim 10, wherein the molar ratio of the gyrase inhibitor to protein is 1.1:1 to 0.5:1.

12. The Gyrase inhibitor-albumin conjugate according to claim 11, wherein the molar ratio of the gyrase inhibitor to the albumin is 1.1:1 to 0.9:1.

13. A Pharmaceutical preparation comprising a gyrase inhibitor-albumin conjugate according to claim 1 as the active substance.

* * * * *